(12) United States Patent
Lynn (10) Patent No.: US 11,214,503 B1
(45) Date of Patent: Jan. 4, 2022

(54) JANITORIAL FILL STATION WITH AQUEOUS OZONE SOLUTION AND PURIFIED WATER FAUCETS

(71) Applicant: Daniel W. Lynn, Omaha, NE (US)

(72) Inventor: Daniel W. Lynn, Omaha, NE (US)

( * ) Notice: Subject to any disclaimer, the term of this patent is extended or adjusted under 35 U.S.C. 154(b) by 0 days.

(21) Appl. No.: 17/384,016

(22) Filed: Jul. 23, 2021

Related U.S. Application Data

(63) Continuation-in-part of application No. 17/325,966, filed on May 20, 2021, now Pat. No. 11,098,910, which is a continuation-in-part of application No. 17/200,799, filed on Mar. 13, 2021, now Pat. No. 11,045,571.

(51) Int. Cl.

| | |
|---|---|
| *C02F 1/78* | (2006.01) |
| *B08B 3/02* | (2006.01) |
| *B01F 3/04* | (2006.01) |
| *B01F 5/04* | (2006.01) |
| *F24F 8/40* | (2021.01) |
| *A61L 9/015* | (2006.01) |

(52) U.S. Cl.
CPC .............. *C02F 1/78* (2013.01); *B01F 3/0446* (2013.01); *B01F 5/0413* (2013.01); *B08B 3/02* (2013.01); *A61L 9/015* (2013.01); *B01F 2003/04886* (2013.01); *C02F 2303/04* (2013.01); *C02F 2307/06* (2013.01); *F24F 8/40* (2021.01)

(58) Field of Classification Search
CPC .... F24F 8/40; A61L 9/015; C02F 1/78; B01F 3/0446
See application file for complete search history.

(56) References Cited

U.S. PATENT DOCUMENTS

| | | |
|---|---|---|
| 6,153,105 A | 11/2000 | Tadlock et al. |
| 6,334,328 B1 | 1/2002 | Brill |
| 6,685,825 B1 | 2/2004 | Chang |
| 8,071,526 B2 | 12/2011 | Lynn |
| 8,075,705 B2 | 12/2011 | Lynn |
| 9,068,149 B2 | 6/2015 | Lynn |
| 9,151,528 B2 | 10/2015 | Erbs et al. |
| 9,174,845 B2 | 11/2015 | Lynn |
| 9,522,348 B2 | 12/2016 | Lynn |
| 9,919,939 B2 * | 3/2018 | Rosko ..................... E03C 1/055 |
| 10,792,625 B2 * | 10/2020 | Talamantez ........... B01F 3/2035 |
| 2002/0070107 A1 | 6/2002 | Usinowicz et al. |
| 2002/0127158 A1 | 9/2002 | Holsclaw et al. |

(Continued)

*Primary Examiner* — Robert A Hopkins
(74) *Attorney, Agent, or Firm* — Nasr Patent Law LLC; Faisal K. Abou-Nasr (57) ABSTRACT

A disclosed system includes one or more ozone generators disposed and a fluid mixer configured to inject ozone generated by the one or more ozone generators into water received from a water source via a water inlet to produce an aqueous ozone solution that is output via an aqueous ozone solution outlet. The aqueous ozone solution outlet is fluidically coupled to a splitter. The system further includes a janitorial fill station with a first faucet fluidically coupled to a first output of the splitter and configured to dispense a first portion of the aqueous ozone solution, a carbon filter fluidically coupled to a second output of the splitter and configured to reduce an ozone concentration of a second portion of the aqueous ozone solution to produce purified water for consumption, and a second faucet fluidically coupled to the carbon filter and configured to dispense the purified water.

10 Claims, 6 Drawing Sheets

(56) References Cited

U.S. PATENT DOCUMENTS

| | | |
|---|---|---|
| 2003/0209502 A1 | 11/2003 | Lacasse et al. |
| 2004/0004042 A1 | 1/2004 | Hadley et al. |
| 2004/0168989 A1 | 9/2004 | Tempest |
| 2009/0142225 A1 | 6/2009 | Tornqvist |
| 2010/0219137 A1 | 9/2010 | Lacasse |
| 2013/0193081 A1 | 8/2013 | Vasiliu et al. |
| 2013/0341285 A1 | 12/2013 | Marion |
| 2014/0027388 A1 | 1/2014 | Constant |
| 2014/0263097 A1 | 9/2014 | Lynn |
| 2016/0251243 A1 | 9/2016 | Lynn |

* cited by examiner

JANITORIAL FILL STATION WITH AQUEOUS OZONE SOLUTION AND PURIFIED WATER FAUCETS

CROSS-REFERENCE TO RELATED APPLICATIONS

The present application is a Continuation-in-Part of U.S. application Ser. No. 17/325,966 filed May 20, 2021 and titled "HVAC DECONTAMINATION SYSTEM WITH REGULATED OZONE OUTPUT BASED ON MONITORED OZONE LEVEL IN AMBIENT AIR," which is a Continuation-in-Part of U.S. application Ser. No. 17/200,799 filed Mar. 13, 2021 and titled "REDUCED NOISE AIR DECONTAMINATOR," all of which are incorporated herein by reference.

TECHNICAL FIELD

The present disclosure relates to janitorial systems.

BACKGROUND

Water intended for potable use (e.g., drinking water), may contain disease-causing organisms, or pathogens, which can originate from the source of the water, from resistance to water treatment techniques, from improper or ineffectual water treatment techniques, or so forth. Pathogens include various types of bacteria, viruses, protozoan parasites, and other organisms. To protect drinking water from disease-causing organisms, or pathogens, water suppliers often add a disinfectant, such as chlorine, to the water. However, disinfection practices can be ineffectual because certain microbial pathogens, such as *Cryptosporidium*, are highly resistant to traditional disinfection practices. Also, disinfectants themselves can react with naturally-occurring materials in the water to form byproducts, such as trihalomethanes and haloacetic acids, which may pose health risks.

A major challenge for water suppliers is how to control and limit the risks from pathogens and disinfection byproducts. It is important to provide protection from pathogens while simultaneously minimizing health risks to the population from disinfection byproducts. Oxidation reduction potential (ORP) can be used for water system monitoring to reflect the antimicrobial potential of the water, without regard to the water quality, with the benefit of a single-value measure of the disinfection potential, showing the activity of the disinfectant rather than the applied dose.

There are a number of systems that generate ORP in water by injecting ozone into the water to create an ozone and water solution. This aqueous ozone solution can be used to disinfect/degrease surfaces. However, because of its ozone content, the aqueous ozone solution may be unsafe for consumption. It would be advantageous to leverage the disinfecting properties of ozone to provide both a cleaning solution and purified water that is safe for consumption.

SUMMARY

Aspects of this disclosure are directed to a system that generates an aqueous ozone solution for cleaning purposes and purified water for consumption. In embodiments, the system includes an enclosure with openings for a water inlet and an aqueous ozone solution outlet. One or more ozone generators are disposed within the enclosure. A fluid mixer may also be disposed within the enclosure, in between the water inlet and the aqueous ozone solution outlet. The fluid mixer may be fluidically coupled to the one or more ozone generators and configured to inject ozone generated by the one or more ozone generators into water received from a water source via the water inlet to produce an aqueous ozone solution (e.g., a water and ozone solution) that is output via the aqueous ozone solution outlet. The aqueous ozone solution outlet is fluidically coupled to a splitter having at least two outputs. The system further includes a janitorial fill station with a first faucet fluidically coupled to a first output of the splitter and configured to dispense a first portion of the aqueous ozone solution, a carbon filter fluidically coupled to a second output of the splitter and configured to reduce an ozone concentration of a second portion of the aqueous ozone solution to produce purified water for consumption, and a second faucet fluidically coupled to the carbon filter and configured to dispense the purified water.

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are example and explanatory only and are not necessarily restrictive of the subject matter claimed.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims.

DETAILED DESCRIPTION

Reference will now be made in detail to the subject matter disclosed, which is illustrated in the accompanying drawings.

Embodiments of this disclosure are directed to a system that generates an aqueous ozone solution for cleaning purposes and purified water for consumption. In addition to outputting purified water that is safe for human consumption, the system can be used for cleansing and/or degreasing hard surfaces such as plastic, glass, ceramic, porcelain, stainless steel, or the like. The system can also be used for cleansing and/or degreasing food service equipment such as food service equipment which may include, but are not limited to, ovens, ranges, fryers, grills, steam cookers, oven stacks, refrigerators, coolers, holding cabinets, cold food tables, worktables, ice machines, faucets, beverage dispensing equipment, beer dispensers, shelving food displays, dish washing equipment, and grease traps.

An ORP value can be used for water system monitoring to reflect the antimicrobial potential of a given sample of water. ORP is measured in millivolts (mV), with typically no correction for solution temperature, where a positive voltage shows a solution attracting electrons (e.g., an oxidizing agent). For instance, chlorinated water will show a positive ORP value whereas sodium sulfite (a reducing agent) loses electrons and will show a negative ORP value. Similar to pH, ORP is not a measurement of concentration directly, but rather of activity level. In a solution of only one active component, ORP indicates concentration. The World Health Organization (WHO) adopted an ORP standard for drinking water disinfection of 650 millivolts. That is, the WHO stated that when the oxidation-reduction potential in a body of water measures 650 (about ⅔ of a volt), the sanitizer in the water is active enough to destroy harmful organisms almost instantaneously. For example, *E. coli, Salmonella, Listeria*, and Staph pathogens have survival times of under 30 seconds when the ORP is above 650 mV, compared against >300 seconds when it is below 485 mV.

An example ORP sensor uses a small platinum surface to accumulate charge without reacting chemically. That charge is measured relative to the solution, so the solution "ground" voltage comes from the reference junction. For example, an ORP probe can be considered a millivolt meter, measuring the voltage across a circuit formed by a reference electrode constructed of silver wire (in effect, the negative pole of the circuit), and a measuring electrode constructed of a platinum band (the positive pole), with the water in-between.

Increasingly, microbial issues are commanding the attention of water treatment operators, regulators, media, and consumers. There are many treatment options to eliminate pathogenic microbes from drinking water. One such option includes ozone (03), an oxidizing agent approved for drinking water treatment by the U.S. Environmental Protection Agency. For instance, ozone is one of the strongest disinfectants approved for potable water treatment capable of inactivating bacteria, viruses, *Giardia*, and *Cryptosporidium*.

The disclosed system may be configured to output an aqueous ozone solution including water with an ORP of about 600 mV to about 1000 mV, with particular embodiments configured to output water having an ORP of about 700 mV to about 900 mV to provide pathogenic control. Additionally, the system may be configured to reduce the surface tension of the water being used to cleanse and/or degrease hard surfaces and equipment by creating an aqueous ozone solution (e.g., a water and ozone solution) wherein the surface tension of the water is reduced from about 72 Millinewtons per meter at 20 degrees Centigrade to about 48-58 Millinewtons per meter at 20 degrees Centigrade to greatly improve the cleansing and/or degreasing qualities thereof.

FIGS. 1 through 6 illustrate a system 100 that generates an aqueous ozone solution for cleaning purposes and purified water for consumption, in accordance with one or more embodiments of this disclosure. The system 100 includes an aqueous ozone solution (AOS) supply unit 200 configured to generate and mix ozone into water in order to output an aqueous ozone solution (e.g., a water and ozone solution). Although the AOS supply unit 200 and system 100 are discussed with regard to applications that employ water to generate an aqueous ozone solution, it is contemplated that the AOS supply unit 200/system 100 may be configured to generate other types of ozonated fluid solutions for the purposes of cleansing, degreasing, decontaminating, and/or fluid treatment.

Figure 1:
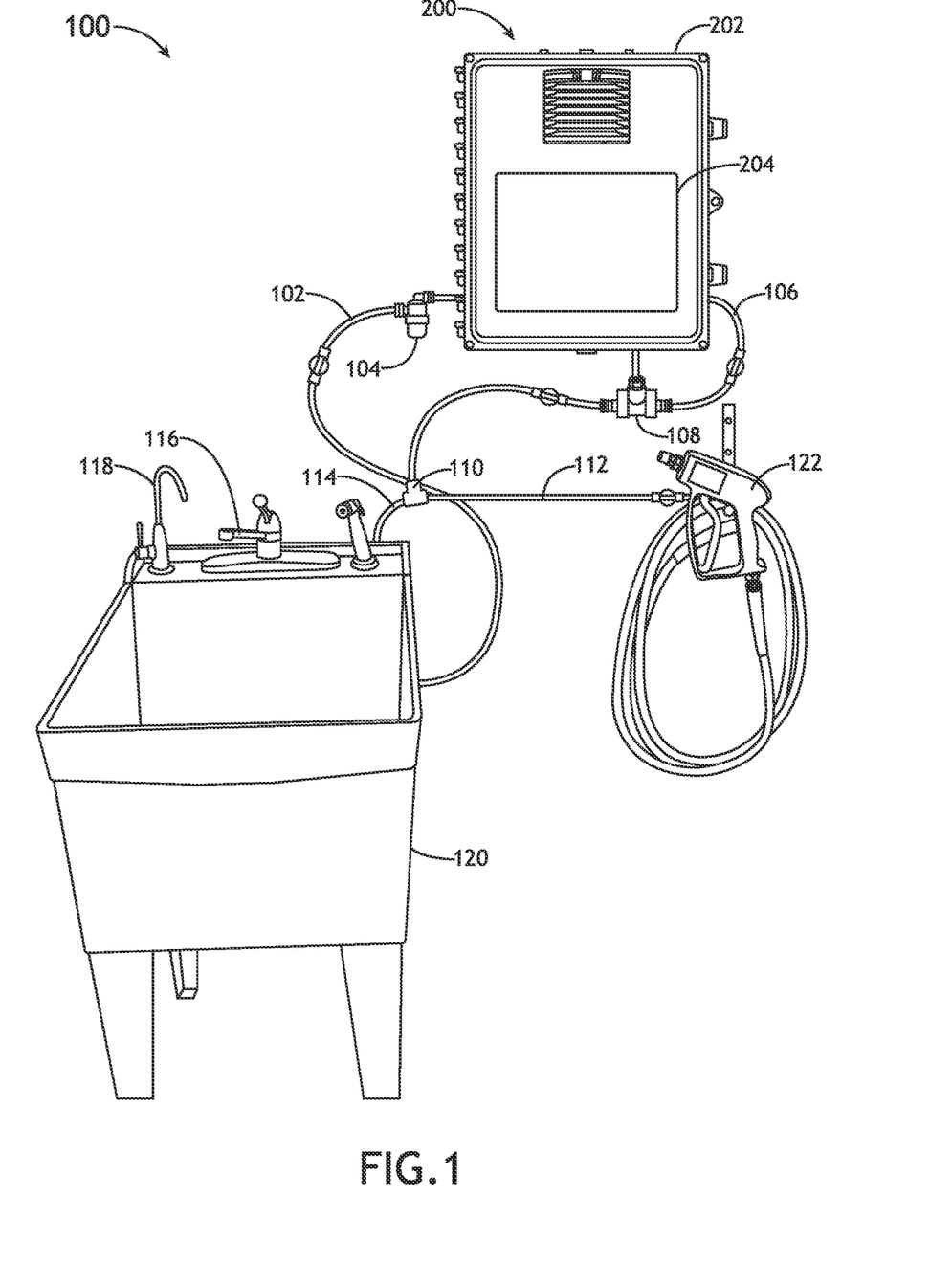
FIG. 1 is a perspective view of a system that generates an aqueous ozone solution for cleaning purposes and purified water for consumption, in accordance with one or more embodiments of this disclosure.

As shown in FIG. 1, the AOS supply unit 200 may include an enclosure 202. The enclosure 202 may have a securable lid/cover 204 that can enclose (e.g., when secured/closed) and provide access to (e.g., when removed/opened) the components housed in an interior portion of the enclosure 202. The securable lid/cover 204 may be secured to the enclosure 202 by a hinge on one side and a latch or fastener on an opposing side. In other embodiments, the securable lid/cover 204 may be secured to the enclosure 202 by one or more fasteners (e.g., screws to mate with bores in the enclosure 202, latches, interference fit fasteners, clipping fasteners, magnetic fasteners, or the like). The enclosure 202 may further include coupling portions to couple with a power cable, a switch to engage or disengage power to the AOS supply unit 200/system 100, an indicator (e.g., a light source), any combination thereof, and so forth.

Figure 2:
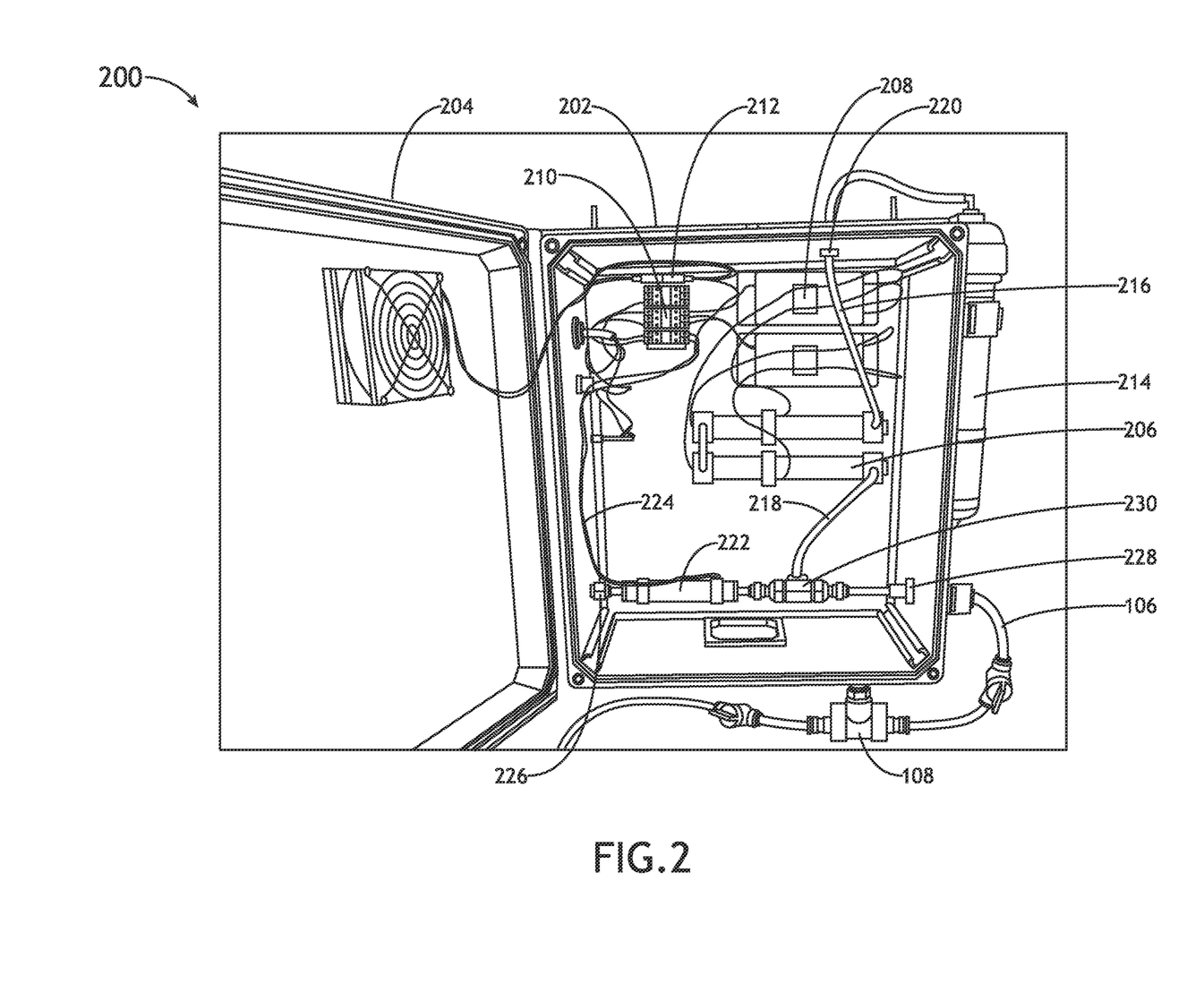
FIG. 2 is a perspective view an aqueous ozone solution supply unit of the system, wherein the aqueous ozone solution supply unit is opened to show its inner components, in accordance with one or more embodiments of this disclosure.

FIG. 2 illustrates the AOS supply unit 200 with the lid/cover 204 opened or removed from the enclosure 202, in accordance with one or more embodiments of this disclosure. As shown in FIG. 2, the enclosure 202 includes one or more air intake ports 220. The AOS supply unit 200 includes a plurality of ozone generators 206 (e.g., two ozone generators 206) disposed within the enclosure 202. The ozone generators 206 are fluidically coupled to the one or more air intake ports 220 of the enclosure 202. For example, the ozone generators 206 may be fluidically coupled to the one or more air intake ports 220 by one or more tubes 216 (e.g., flexible tubing, pipes, etc.). One or more controllers 208 (e.g., two controllers 208) may also be disposed within the enclosure 202. The one or more controllers 208 may be communicatively coupled (e.g., electrically coupled and/or data linked) to the ozone generators 206.

In embodiments, each of the ozone generators 206 may include a corona discharge tube configured to use oxygen supplied via the one or more air intake ports 220 to generate ozone, such as through splitting of oxygen molecules in the air through electrical discharge caused by supplying power to a dielectric material within the corona discharge tube. For example, each ozone generator 206 may include an input port that is fluidically coupled to an air intake port 220 and configured to convert oxygen from incoming air into ozone. The ozone generators 206 may be powered by a power source 212 (e.g., a 120V/240V power supply unit). A power signal from power source 212 may be transformed via a transformer suitable for applying the voltage to the dielectric within the corona discharge tube of the ozone generator 206. For example, a transformer may be coupled to or integrated within a controller 208 for each ozone generator 206 or one controller 208 that controls a plurality of ozone generators 206. In some embodiments, each controller 208 includes a transformer and/or a logic circuit (e.g., processor) that is programmed to selectively activate or deactivate one or more connected ozone generators 206. In other embodiments, each controller 208 is simply a transformer that passively activates one or more connected ozone generators 206 when power is supplied to the controller 208 and deactivates the one or more connected ozone generators 206 when the controller 208 is disconnected from power. The AOS supply unit 200 may include a relay 210 (e.g., a switchboard with analog or digital logic circuits) that controls distribution of power and/or communication signals within the AOS supply unit 200. For example, the relay 210 may be connected to the power source 212, a power switch, an indicator, the one or more controllers 208 and/or ozone generators 206, and any sensors/switches (e.g., flow switch 222 and/or ORP monitor 108) of the AOS supply unit 200/system 100.

In some embodiments, the ozone generators 206 may be operated at 110 volts/60 Hz and have an operating frequency of about 450 kHz and 550 kHz, with a power rating of less than about 15 watts, and with a unit performance for electrical consumption of about 32 watts. For example, the ozone generators 206 may have an operating frequency of about 480 kHz. Further, the ozone generators 206 can be provided according to ISO 9001 CE standards.

Each of the ozone generators 206 may be configured to produce from about 800 mg ozone per hour to about 1200 mg ozone per hour, although other ranges may be appropriate depending on the application. In some embodiments, each of the ozone generators 206 produces about 1000 mg ozone per hour. The ozone generators 206 may include other methods and systems for generating ozone, including but not limited to, electrochemical cells configured to generate ozone from water by placing an anode and a cathode in contact with opposite sides of a proton exchange membrane (PEM), and supplying power to the cell, whereby water flowing over the surface of the anode breaks down into hydrogen atoms and oxygen atoms that assemble to form $O_3$ (ozone).

The AOS supply unit 200 may further include one or more air dryers 214 (or filters), which may be externally coupled to the enclosure 202. The one or more air dryers 214 are configured to remove moisture from air before the air is supplied to the ozone generators 206 through the one or more air intake ports 220. The one or more air dryers 214 may be configured to dry the air to a minus dew point by removing water vapor or moisture therefrom, where the water could inhibit the production of ozone by the ozone generators 206.

In some embodiments, the system 100 may further include an oxygen concentrator configured to supply oxygen-enriched air to the one or more air intake ports 220 of the AOS supply unit 200. For example, the oxygen concentrator may be configured to direct the oxygen-enriched air through the one or more air dryers 214. The oxygen concentrator may also remove moisture from the air. In this regard, the incoming air may undergo two drying stages. The oxygen concentrator may be fluidically coupled to the AOS supply unit 200 (e.g., to the one or more air dryers 214 and/or one or more air intake ports 220) by one or more tubes (e.g., flexible tubing, pipes, etc.) for transferring oxygen-enriched air from the oxygen concentrator to the AOS supply unit 200.

In some embodiments, each air dryer 214 includes or is coupled to an air compressor. The pressure provided by the compressor can vary depending on the water pressure supplied to the AOS supply unit 200/system 100, where the pressure applied by the compressor can be balanced based on the flow rate of air received by the ozone generators 206 via the one or more air intake ports 220 and the water pressure supplied to the AOS supply unit 200/system 100 to obtain a particular ORP of the aqueous ozone solution output by the AOS supply unit 200/system 100. For example, the compressor may be configured to compress the filtered air at least about 15 KPa (e.g., more particularly at a pressure of 18 KPa or about 2.6 psi) to provide a gas throughput in each ozone generator 206 of about 8 SCFH (standard cubic feet per hour), where the water pressure in each fluid path is about 50 psi to 55 psi (e.g., a reasonable rating for many residential and commercial facilities), to provide an ORP in the water at the outlet of at least about 600 mV (e.g., about 600 mV to about 1000 mV, more particularly about 700 mV to about 900 mV). At these pressures, each ozone generator 206 has a residence time of the gas of about three seconds. The pressure applied by the compressor can affect the rate at which the gas flows through an ozone generator 206, which can affect contact time of the air with the components of the ozone generator 206, which can also affect mass gas transfer rates within the ozone generator 206.

The AOS supply unit 200 may include a plurality of ozone generators 206. For example, in the embodiment illustrated FIG. 2, the AOS supply unit 200 includes two ozone generators 206. As shown in FIG. 2, the ozone generators 206 may be fluidically connected in series with one other. Such configurations may provide increased ozone output and/or backup ozone generators 206 in case of malfunction or inoperability of one or more of the other ozone generators 206. On average, each ozone generator 206 may have an operating life of about 10,000 working hours. In some embodiments of the AOS supply unit 200, two or more ozone generators 206 may be connected in parallel to achieve a higher rate of ozone throughput per line.

The AOS supply unit 200 may include a fluid mixer 230 fluidically coupled to the one or more ozone generators 206 by one or more tubes 218 (e.g., flexible tubing, pipes, etc.) for transferring ozone from the one or more ozone generators 206 to the fluid mixer 230. In some embodiments, the fluid mixer 230 is disposed within the enclosure 202 between a water inlet 226 and an AOS outlet 228. The fluid mixer 230 may be configured to introduce/inject ozone generated by the ozone generators 206 into water flowing between the water inlet 226 and the AOS outlet 228. In this manner, the fluid mixer 230 mixes the ozone from the ozone generators 206 with the water flowing into the AOS supply unit 200 to produce an aqueous ozone solution that is output via the AOS outlet 228.

The fluid mixer 230 may be a multi-port coupler including an inlet, an outlet, and an ozone input port between the inlet and the outlet. The multi-port coupler may simply be pipe/tube fittings with an ozone input port formed therein, 3-way pipe/tube fittings, or the like. In some embodiments, the multi-port coupler includes a venturi. A venturi can include an injector venturi design (e.g., a "T" design), where the venturi is coupled between the inlet and the outlet, and where ozone is introduced to the venturi through another port (i.e., the ozone input port) positioned perpendicular to the flow path of the water (from the inlet to the outlet). During operation, ozone generated by the ozone generators 206 is drawn into the venturi and mixed with the water stream flowing from the inlet to the outlet. A pressure differential between the inlet and the outlet may serve to facilitate drawing the ozone into the venturi and to facilitate mixing of the ozone and the water. In some embodiments, a pressure differential greater than 20 psi inlet over outlet (e.g., at least a 20 psi difference between the inlet and the outlet, with pressure higher at the water inlet) is provided to generate negative suction in the venturi to thereby draw in the generated ozone, while assuring the energy for water flow and pressure for operation of the venturi.

In order to further increase effectiveness of the mixing process delivered by the venturi, the aqueous ozone solution may pass through an in-line mixer coupled between the venturi and the outlet. In this regard, the fluid mixer 230 may include a combination of a venturi and an in-line mixer, or another type of multi-port coupler with an in-line mixer. The in-line mixer can facilitate further breaking or mixing of ozone bubbles already introduced to the water to generate a mixture (or solution) of water and substantially uniform-sized ozone bubbles. The small uniform-size ozone bubbles can adhere to each other to lower the surface tension of the aqueous ozone solution. For example, water can have a surface tension of about 72 Millinewtons, whereas the solution of water and substantially uniform-sized ozone bubbles can have a surface tension of about 48-58 Millinewtons. In embodiments, the in-line mixer has an internal diameter that equals an internal diameter of the output port of the venturi to which the in-line mixer is coupled. The same internal diameter can provide an uninterrupted transition of the fluid flowing from the venturi to the in-line mixer, such as to maintain a vortex action or mixing action of the water and the ozone bubbles. The in-line mixer also provides increased contact time between the water and ozone bubbles and can facilitate preparation of uniform ozone bubble size. In some embodiments, the in-line mixer has a length of about two inches downstream from the venturi, which can allow sufficient time for the velocity of the vortex action caused by the pressure differential of the venturi to crush the gaseous bubbles entrained in the solution into uniformed size bubbles. The in-line mixer can also reintroduce undissolved gas back into the solution resulting in increased efficiency as well as reduced off-gas at the point of application. The in-line mixer can include multiple chambers through which the aqueous ozone solution flows. The size of the chambers can be determined based on the water flow (e.g., throughput), gas mixing, and desired time exposure. In some embodiments, the AOS supply unit 200 produces a stream of aqueous ozone solution at the AOS outlet 228 having a molar concentration of ozone of at least 20%, or more particularly at least 25%, far surpassing previous systems that have mass gas transfer rates of less than 10%.

The AOS supply unit 200 may further include or may be coupled with a flow switch 222 that is configured to detect water flow through the AOS supply unit 200/system 100. As shown in FIG. 2, the flow switch 222 may be disposed within the enclosure 202. For example, the flow switch 222 may be fluidically coupled in-line with the fluid mixer 230, between the water inlet 226 and the AOS outlet 228. In some embodiments, the water inlet 226 and the AOS outlet 228 are located on opposite sides of the enclosure 202, allowing for a linear (e.g., horizontal) flow path through the enclosure 202. In other embodiments, the flow switch 222 may be external to the enclosure 202 and/or at a distance from the enclosure 202. For example, the flow switch 222 may be coupled to any of the fluid paths for water/AOS flow through the system 100 (e.g., water input line 102, water output line 106, splitter 110, etc.).

The flow switch 222 can be configured to provide electric signals indicative of water/AOS flow through the AOS supply unit 200/system 100. For example, the flow switch 222 may be a mechanical flow switch/sensor, electromagnetic flow switch/sensor, pressure-based flow switch/sensor, optical flow switch/sensor, or the like, configured to provide an electric signal indicative of a flow of fluid (e.g., water/AOS) through the AOS supply unit 200/system 100. In some embodiments, the flow switch 222 may include solenoid-based flow switches/sensors, such as to avoid significant restriction of flow through the AOS supply unit 200/system 100.

In embodiments, the flow switch 222 is configured to transmit one or more control signals to the one or more controllers 208 in response to sensing a flow of water/AOS through the AOS supply unit 200/system 100. In response to receiving the one or more control signals, the one or more controllers 208 are configured to cause the ozone generators 206 to generate ozone. In some embodiments, the controllers 208 are transformers that become activated by control signals (e.g., status/power signals) transmitted by the flow switch 222 in response to sensing a flow of water/AOS. In other embodiments, the controllers 208 may further include microprocessors, microcontrollers, or other programmable logic devices. In such embodiments, the one or more controllers 208 may be configured (e.g., programmed) to activate the transformers and/or ozone generators 206 in response to the control signals (e.g., status signals) and possibly based on other sensor signals being monitored by the one or more controllers 208.

The flow switch 222 may be communicatively coupled to the one or more controllers 208 by one or more connectors 224 (e.g., wires, cables, optical fibers, etc.) for transmitting signals between the flow switch 222 and the one or more controllers 208. As shown in FIG. 2, the AOS supply unit 200 may include a relay 210 that distributes the incoming signals to the one or more controllers 208. In embodiments, the flow switch 222 is communicatively coupled to the relay 210 by the one or more connectors 224. The relay 210 may be configured to transmit the control signals from the flow switch 222 to the controllers 208, whereby the controllers 208 are programmed to activate the ozone generators 206 in response to receiving one or more control signals indicating a flow of water/AOS through the AOS supply unit 200/system 100. Alternatively, the relay 210 itself may be configured to connect the controllers/transformers 208 to power (or to directly power the ozone generators 206 if no controllers/transformers 208 are present) in response to receiving one or more control signals indicating a flow of water/AOS through the AOS supply unit 200/system 100. In further embodiments, the AOS supply unit 200 may include a wireless communication interface (e.g., wireless receivers, transmitters, and/or transceivers) for receiving signals from the flow switch 222. For example, the flow switch 222 and one or more of the controllers 208 and/or relay 210 may include wireless communication interfaces for sending/receiving wireless communication/control signals.

The AOS supply unit 200 may be configured to dispense an aqueous ozone solution (e.g., a water and ozone solution) having an ORP of between 600 mV and 1000 mV to provide pathogenic control without introduction of harsh treatment chemicals, such as chlorine. After operation of the AOS supply unit 200, the output aqueous ozone solution can provide removal of organic and inorganic compounds, can provide removal of micro-pollutants (e.g., pesticides), can provide enhancement of the flocculation/coagulation decantation process, can provide enhanced disinfection while reducing disinfection by-products, can provide odor and taste elimination of the treated water, and so forth. The solubility of ozone in water is quite good, about 10 to 15 times greater than for oxygen under normal drinking water treatment conditions. About 0.1 to 0.6 liters of ozone will dissolve in one liter of water. The size of the ozone gas bubbles can influence gas transfer characteristics. In some embodiments, the fluid mixer 230 generates an ozone bubble size of about 2 to about 3 microns. For instance, micro-bubbles can be produced by the fluid mixer 230 and/or sheared into uniformed micro-size bubbles as the solution passes through the fluid pathways.

Corona discharge ozone can be used virtually anywhere. Since ozone is made on site, as needed and where needed, there is no need to ship, store, handle or dispose of it, nor any containers associated with shipping, storing, handling, and disposing a treatment chemical, as is the situation with most chemicals utilized in water treatment.

The AOS supply unit 200 may be configured to provide indications pertaining to the operation status of the AOS supply unit 200/system 100, such as to ensure proper operation, or to provide an indication regarding a need for adjustment, servicing, or maintenance. For example, the flow switch 222 may be configured to send the signal to an indicator located on an exterior of the enclosure 202 to provide a visual, tactile, or audible indication that fluid (e.g., water/AOS) is flowing through the AOS supply unit 200/system 100. In some embodiments, the indicator is a light source (e.g., an LED) configured to illuminate upon receiving a signal from the flow switch 222. The indicator may also be coupled to a sensor (e.g., a relay) configured to measure that a voltage is applied to ozone generators 206. When a proper voltage is applied to the ozone generators 206, the sensor can send a signal to the indicator. In some embodiments, the indicator will provide a visual, tactile, or audible indication when each sensor and the flow switch 222 provide their respective signals to the indicator. For example, the relay 210 can be coupled to the power source 212 and the flow switch 222. The relay 210 may be configured to send an activation signal to the indicator when the power source 212 is providing power to the ozone generators 206 and when the flow switch 222 provides one or more signals regarding fluid flow through the AOS supply unit 200/system 100. In such a configuration, the indicator can verify that the AOS supply unit 200/system 100 is operating under design conditions (e.g., having an active flow of water, and having a sufficient power supply to the ozone generators 206).

In some embodiments, the system 100 (or AOS supply unit 200) may include an in-line ORP monitor 108 (e.g., ORP sensor/meter) positioned to measure the ORP of the aqueous ozone solution the AOS outlet 228, coupled within a distribution line, or the like. The in-line ORP monitor 108 can be coupled with the relay 210, such that the in-line ORP monitor 108 provides a signal to the relay 210 upon detection of a desired ORP or range of ORPs (e.g., at least 600 mV, at least 650 mV, at least 700 mV, at least 750 mV, at least 800 mV, at least 850 mV, at least 900 mV, at least 950 mV, etc.). The relay 210 can then provide an activation signal to the indicator upon proper functioning of the AOS supply unit 200/system 100 (e.g., when the power source 212 is providing power to the ozone generators 206, when the flow switch 222 provides one or more signals regarding fluid flow through the AOS supply unit 200/system 100, and when the in-line ORP monitor 108 detects a desired ORP of the aqueous ozone solution generated by the AOS supply unit 200/system 100). When the indicator is not activated, this can provide an indication that a component or components of the AOS supply unit 200/system 100 may need adjustment, servicing, or maintenance. Alternatively, the AOS supply unit 200/system 100 can be configured to activate the indicator upon failure of one or more of the components of the AOS supply unit 200/system 100 (e.g., no power supplied to the ozone generators 206, no flow of water detected by the flow switch 222, or an out of range ORP detected by the in-line ORP monitor 108).

By providing an ORP of between 600 mV and 1000 mV with the AOS supply unit 200/system 100, the output aqueous ozone solution can be utilized to destroy various pathogens, including, but not limited to, algae (e.g., blue-green), bacteria (e.g., *Aeromonas* & Actinomycetes, *Bacillus*, Campylobacters, *Clostridium botulinum, Escherichia coli* (*E. coli*), *Flavobacterium, Helicobacter* (*pylori*), Heterotrophic Bacteria, *Legionella pneumophila, Micrococcus, Mycobacterium tuberculosis, Pseudomonas aeruginosa, Salmonella, Shigella* shigellosis (dysentery), *Staphylococcus* sp, *albus, aureus, Streptococcus, Vibrio: alginolyticus, anguillarium, parahemolyticus, Yersinia enterocolitica*), fungi, molds, yeasts, mold spores, nematodes, protozoa (e.g., *Acanthamoeba* & *Naegleria*, Amoeboe Trophozoites, *Cryptosporidium, Cyclospora, Entamobea* (*histolytica*), *Giardia lamblia, Giardia muris, Microsporidium, N. gruberi*), trematodes, viruses (e.g., Adenovirus, Astrovirus, Cailcivirus, Echovirus, Encephalomyocarditis, Enterovirus, coxsachie, poliovirus, Hepatitis A, B and C, Myxovirus influenza, Norwalk, Picobirnavirus, Reovirus, Rotavirus).

In some implementations, incoming water may have a surface tension of about 72 Millinewtons per meter at 20° C. as it enters the AOS supply unit 200/system 100. The AOS supply unit 200/system 100 may be configured to reduce the surface tension of the water in the resulting aqueous ozone solution to about 48-58 Millinewtons per meter at 20° C. The reduced surface tension of the water enables the aqueous ozone solution being sprayed onto the hard surfaces and equipment to remove grease more effectively from hard surfaces and equipment since ozonated fluid is more capable of loosening and disintegrating any biofilm on the hard surfaces or equipment. The reduced surface tension of the water in the aqueous ozone solution better enables the cleansing of the hard surfaces and equipment since it more easily penetrates foreign material on the hard surfaces and equipment.

The aqueous ozone solution can be used for a variety of applications including, but not limited to: cleansing and/or degreasing hard surfaces such as plastic, glass, ceramic, porcelain, stainless steel, or the like; cleansing and/or degreasing equipment such as food service equipment such as ovens, ranges, fryers, grills, steam cookers, oven stacks, refrigerators, coolers, holding cabinets, cold food tables, worktables, ice machines, faucets, beverage dispensing equipment, beer dispensers, shelving food displays, dish washing equipment, grease traps, or the like; and/or cleansing and/or degreasing HVAC or plumbing systems such as roof top units, air scrubbers, humidifiers, water heaters, pumps, or the like.

Referring again to FIG. 1, the system 100 includes a water input line 102 configured to supply water from a water source (e.g., a conventional water main/supply line, or the like) to the AOS supply unit 200. For example, the water input line 102 may be fluidically coupled to the water inlet 226 of the AOS supply unit 200. In some embodiments, the water input line 102 includes or is coupled to a sediment filter 104 configured to remove particulates (e.g., sand, silt, dirt, rust, etc.) from water before the water enters the AOS supply unit 200. The AOS supply unit 200 is configured to produce an aqueous ozone solution (as described above) by mixing ozone into the water. The aqueous ozone solution is then output from the AOS supply unit 200 via the AOS outlet 228 which may be coupled to an AOS output line 106. In some embodiments, the AOS output line 106 includes or is coupled to the ORP monitor 108.

Figure 4:
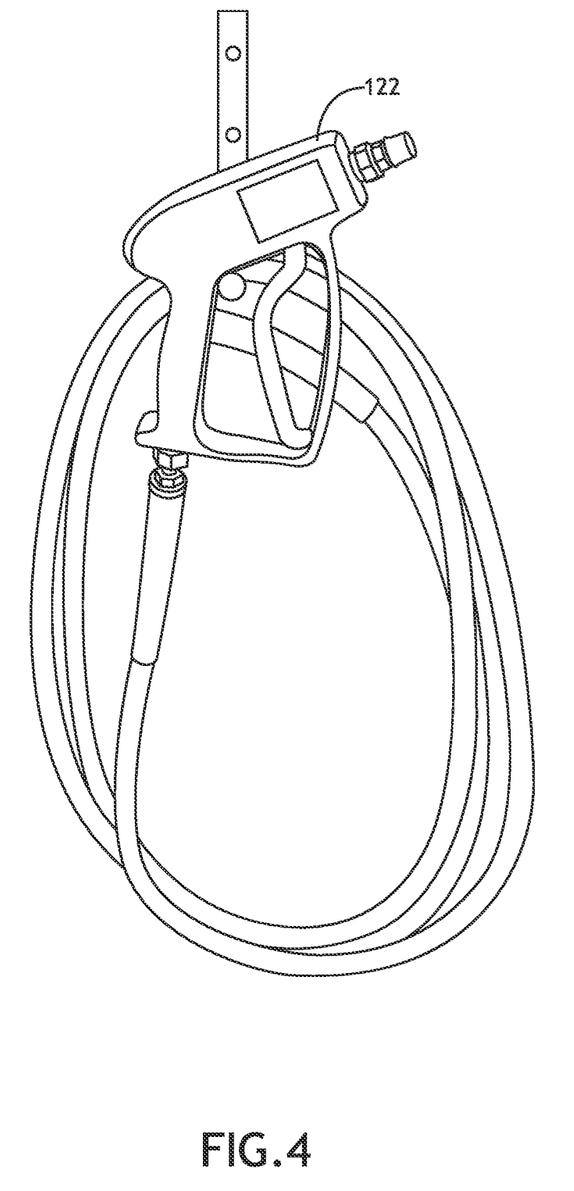
FIG. 4 is a perspective view of a spray gun of the system, in accordance with one or more embodiments of this disclosure.

In some embodiments, the system 100 includes a splitter 110 fluidically coupled to the AOS outlet 228 of the AOS supply unit 200 via the AOS output line 106. The splitter 110 may be configured to fluidically couple the AOS outlet 228 with a janitorial fill station 120 via AOS supply line 114 and to a spray gun 122 via AOS supply line 112. The spray gun 112 may be configured to dispense a portion of the aqueous ozone solution received via splitter 110 from the AOS outlet 228 to disinfect or degrease surfaces or articles in proximity of the AOS supply unit 200 (e.g., within 50 feet of the AOS supply unit 200). An example embodiment of the spray gun 122 is illustrated in FIG. 4.

Figure 3:
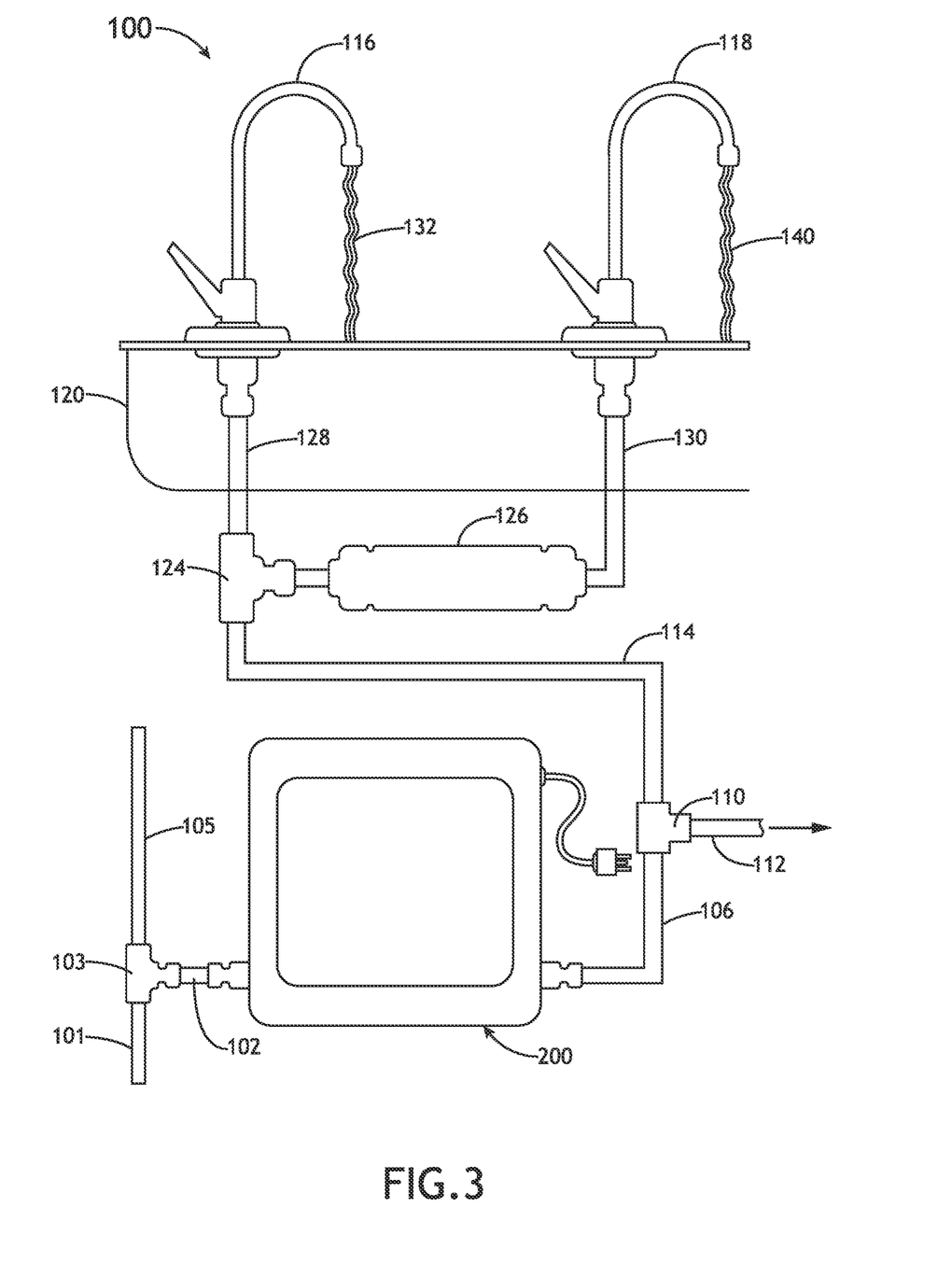
FIG. 3 is schematic illustration of the system, in accordance with one or more embodiments of this disclosure.

Referring now to FIGS. 1 and 3, the janitorial fill station 120 may include a faucet 116 configured to dispense a portion of the aqueous ozone solution for various cleansing (e.g., disinfecting/degreasing) applications and another faucet 118 configured to dispense purified water produced by filtering a portion of the aqueous ozone solution. As shown in FIG. 3, the system 100 may include another splitter 124 fluidically coupled to splitter 110 via AOS supply line 114. Alternatively, splitter 124 may be directly coupled to the AOS output line 106 if splitter 110, AOS supply line 112 and the spray gun 122 are not present.

In embodiments, splitter 124 is configured to direct a portion of the aqueous ozone solution output by the AOS supply unit 200 to faucet 116 via AOS supply line 128, whereby faucet 116 is configured to dispense aqueous ozone solution 132 for various cleansing (e.g., disinfecting/degreasing) applications. The splitter 124 is further configured to direct a portion of the aqueous ozone solution to a carbon filter 126 (e.g., an activated carbon filter) that is configured to reduce an ozone concentration of the aqueous ozone solution to produce purified water for consumption. Faucet 118 is fluidically coupled to the carbon filter 126 by purified water supply line 130 and is configured to dispense purified water 140 that is safe for consumption. In other embodiments, faucet 118 may include a built-in carbon filter 126.

In some embodiments, the system 100 may further include multi-port valve 103 (e.g., a Tee Stop Valve) configured to couple the water supply line 102 with the water source (e.g., main line 101). The multi-port valve 103 may be further configured to couple another water supply line 105 with the water source (e.g., main line 101) to deliver unfiltered water to another faucet or other equipment when aqueous ozone solution and purified water are not required. This may be useful for applications that require higher water pressure (e.g., to rinse off dirt, quickly fill a bucket, etc.). In this regard, the system 100 may be configured to output aqueous ozone solution 132 via faucet 116, purified water 140 via faucet 118, and optionally aqueous ozone solution via spray gun 122 and/or unfiltered water via water supply line 105 (equipped with another faucet, spray gun, or the like).

Figure 5:
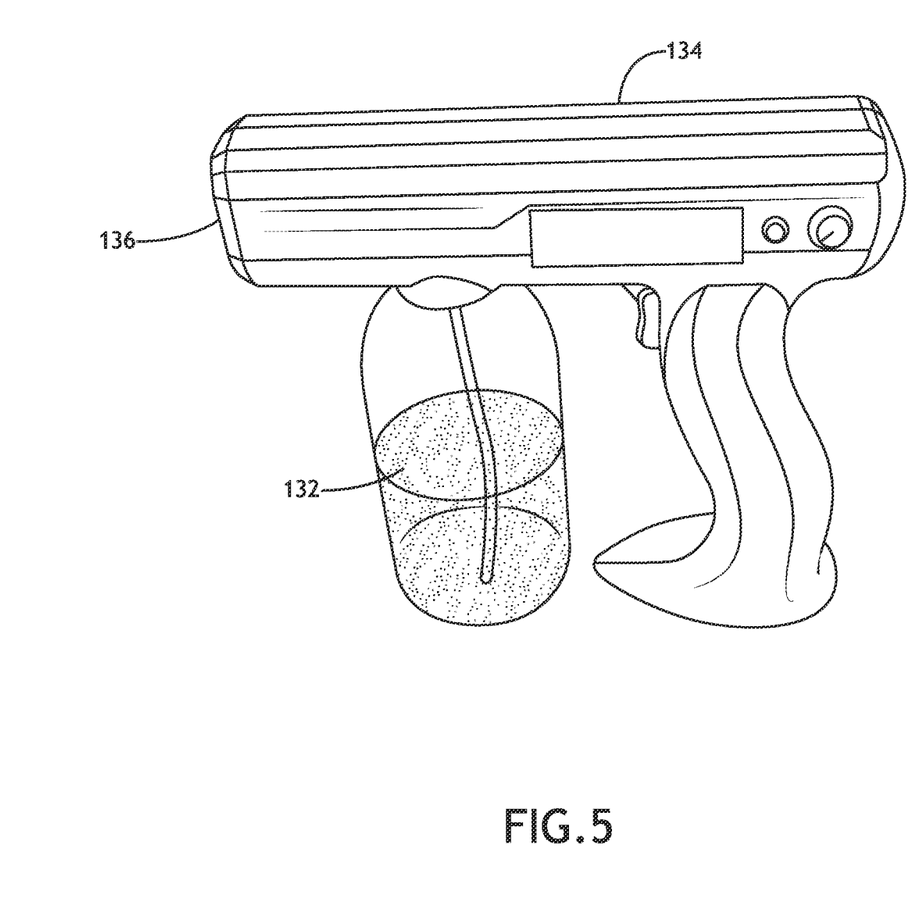
FIG. 5 is a perspective view of a portable electric sprayer of the system, in accordance with one or more embodiments of this disclosure.
Figure 6:
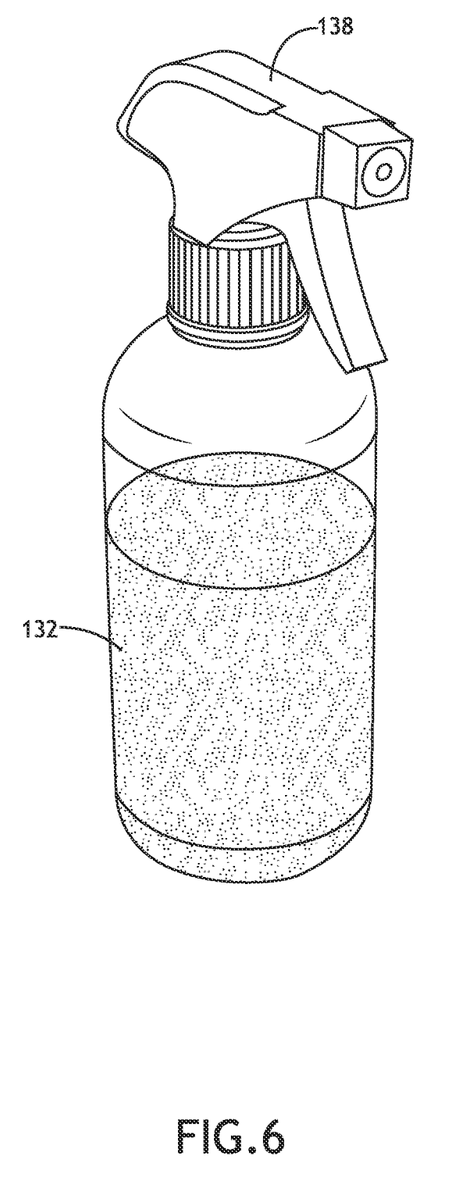
FIG. 6 is a perspective view of a spray bottle of the system, in accordance with one or more embodiments of this disclosure.

In addition to outputting aqueous ozone solution 132 via faucet 116, the system 100 may include one or more portable sprayers configured to administer the aqueous ozone solution 132 for cleansing and/or disinfecting purposes. As shown in FIG. 5, the system 100 may include a portable electric sprayer 134 filled with a portion of the aqueous ozone solution 132. The portable electric sprayer 134 may be configured to release a spray, a mist, or a foam formed from the aqueous ozone solution 132 to disinfect or degrease a surface. In some embodiments, the portable electric sprayer 134 is a portable electric mist sprayer including a porous nozzle 136 configured to release a mist formed from the aqueous ozone solution 132. For example, the porous nozzle 136 may enable the portable electric sprayer 134 to nebulize the aqueous ozone solution 132 so it can be sprayed as a fine mist across a surface to disinfect/degrease the surface or within an enclosed area to disinfect the air. As shown in FIG. 6, the system 100 may additionally/alternatively include a spray bottle 138 filled with a portion of the aqueous ozone solution 132. The spray bottle 138 may be configured to release a spray, a mist, or a foam formed from the aqueous ozone solution to disinfect or degrease a surface. In some embodiments, the spray bottle 138 can also be equipped with a porous nozzle configured to release a mist formed from the aqueous ozone solution 132. The system 100 may further include any other janitorial tools (e.g., bucket and mop, carpet cleaner, etc.) that typically employ water and/or cleaning solutions to disinfect and/or degrease surfaces, wherein the water and/or cleaning solutions can be replaced with aqueous ozone solution 132 to obtain improved cleaning performance and efficiency.

Although the invention has been described with reference to embodiments illustrated in the attached drawings, equivalents or substitutions may be employed without departing from the scope of the invention as recited in the claims. Components illustrated and described herein are examples of devices and components that may be used to implement embodiments of the present invention and may be replaced with other devices and components without departing from the scope of the invention. Furthermore, any dimensions, degrees, and/or numerical ranges provided herein are to be understood as non-limiting examples unless otherwise specified in the claims.

What is claimed is:

1. A system that generates an aqueous ozone solution for cleaning purposes and purified water for consumption, the system comprising:
    an enclosure with openings for a water inlet and an aqueous ozone solution outlet;
    one or more ozone generators disposed within the enclosure;
    a fluid mixer disposed within the enclosure, in between the water inlet and the aqueous ozone solution outlet, the fluid mixer being fluidically coupled to the one or more ozone generators and configured to inject ozone generated by the one or more ozone generators into water received from a water source via the water inlet to produce an aqueous ozone solution that is output via the aqueous ozone solution outlet;
    a first splitter fluidically coupled to the aqueous ozone solution outlet;
    a spray gun fluidically coupled to the first splitter and configured to dispense a first portion of the aqueous ozone solution received via the first splitter from the aqueous ozone solution outlet to disinfect or degrease surfaces or articles in proximity of the aqueous ozone solution outlet;
    a second splitter fluidically coupled to the first splitter; and
    a janitorial fill station including:
        a first faucet fluidically coupled to the second splitter and configured to dispense a second portion of the aqueous ozone solution received via the first and second splitters from the aqueous ozone solution outlet;
        a carbon filter fluidically coupled to the second splitter and configured to reduce an ozone concentration of a third portion of the aqueous ozone solution received via the first and second splitters from the aqueous ozone solution outlet to produce purified water for consumption; and
        a second faucet fluidically coupled to the carbon filter and configured to dispense the purified water.

2. The system of claim 1, further comprising:
a portable electric sprayer filled with the second portion of the aqueous ozone solution dispensed by the first faucet, the portable electric sprayer configured to release a spray, a mist, or a foam formed from the second portion of the aqueous ozone solution to disinfect or degrease a surface.

3. The system of claim 2, wherein the portable electric sprayer is a portable electric mist sprayer including a porous nozzle configured to release a mist formed from the second portion of the aqueous ozone solution to disinfect or degrease a surface.

4. The system of claim 3, wherein the portable electric mist sprayer is configured to nebulize the second portion of the aqueous ozone solution.

5. The system of claim 1, further comprising:
a spray bottle filled with the second portion of the aqueous ozone solution dispensed by the first faucet, the spray bottle configured to release a spray, a mist, or a foam formed from the second portion of the aqueous ozone solution to disinfect or degrease a surface.

6. The system of claim 1, wherein the fluid mixer comprises a venturi.

7. The system of claim 1, further comprising:
a flow switch disposed within the enclosure, in between the water inlet and the aqueous ozone solution outlet, the flow switch configured to generate a signal indicative of water flow between the water inlet and the aqueous ozone solution outlet.

8. The system of claim 7, wherein the one or more ozone generators are configured to be selectively activated in response to the signal generated by the flow switch.

9. The system of claim 1, further comprising:
an air dryer externally coupled to the enclosure, the air dryer configured to remove moisture from air before the air is supplied to the one or more ozone generators to generate ozone.

10. The system of claim 1, further comprising:
an ORP monitor disposed between the aqueous ozone solution outlet and the splitter, the ORP monitor configured to detect an ORP of the aqueous ozone solution aqueous ozone solution that is output via the aqueous ozone solution outlet.

* * * * *